(12) United States Patent
Machida

(10) Patent No.: US 11,502,046 B2
(45) Date of Patent: Nov. 15, 2022

(54) SEMICONDUCTOR CHIP

(71) Applicant: Hitachi, Ltd., Tokyo (JP)

(72) Inventor: Shuntaro Machida, Tokyo (JP)

(73) Assignee: HITACHI, LTD., Tokyo (JP)

( * ) Notice: Subject to any disclaimer, the term of this patent is extended or adjusted under 35 U.S.C. 154(b) by 243 days.

(21) Appl. No.: 16/928,909

(22) Filed: Jul. 14, 2020

(65) Prior Publication Data

US 2021/0043584 A1 Feb. 11, 2021

(30) Foreign Application Priority Data

Aug. 8, 2019 (JP) .............................. JP2019-146036

(51) Int. Cl.
*H01L 29/82* (2006.01)
*H01L 23/00* (2006.01)
*B06B 1/02* (2006.01)
*B81B 3/00* (2006.01)
*A61B 8/00* (2006.01)

(52) U.S. Cl.
CPC .......... *H01L 23/562* (2013.01); *B06B 1/0292* (2013.01); *B81B 3/0072* (2013.01); *A61B 8/445* (2013.01); *B81B 2201/0271* (2013.01)

(58) Field of Classification Search
CPC ... H01L 23/562; B06B 1/0292; B81B 3/0072; B81B 2201/0271
See application file for complete search history.

(56) References Cited

U.S. PATENT DOCUMENTS

| 2010/0109151 | A1* | 5/2010 | Fujimura | .......... H01L 23/49833 257/701 |
|---|---|---|---|---|
| 2012/0107999 | A1 | 5/2012 | Fan | |
| 2012/0109255 | A1 | 5/2012 | Fan | |
| 2012/0109295 | A1 | 5/2012 | Fan | |
| 2012/0109296 | A1 | 5/2012 | Fan | |
| 2012/0279060 | A1 | 11/2012 | Fan | |
| 2012/0283799 | A1 | 11/2012 | Fan | |
| 2014/0080257 | A1 | 3/2014 | Fan | |
| 2016/0074659 | A1 | 3/2016 | Fan | |

FOREIGN PATENT DOCUMENTS

| JP | H11-204566 A | 7/1999 |
|---|---|---|
| WO | 2012154211 A1 | 11/2012 |

OTHER PUBLICATIONS

Office Action dated Aug. 9, 2022 in Japanese Application No. 2019-146036.

* cited by examiner

*Primary Examiner* — Samuel A Gebremariam
(74) *Attorney, Agent, or Firm* — Miles & Stockbridge, P.C.

(57) ABSTRACT

Provided is a semiconductor chip, including: a semiconductor substrate; a thin film formed on the semiconductor substrate, the thin film having internal stress; and a semiconductor device formed on the semiconductor substrate that has the thin film formed thereon, wherein the semiconductor chip warps due to the internal stress of the thin film.

6 Claims, 10 Drawing Sheets

TOP SURFACE

AA' CROSS-SECTION

BB' CROSS-SECTION

CHIP WARPED DUE TO INTERNAL STRESS OF THIN FILM

TOP SURFACE

AA' CROSS-SECTION

BB' CROSS-SECTION

TOP SURFACE

AA' CROSS-SECTION

BB' CROSS-SECTION

TOP SURFACE

AA' CROSS-SECTION

BB' CROSS-SECTION

TOP SURFACE

AA' CROSS-SECTION

REDUCE THICKNESS OF SEMICONDUCTOR SUBSTRATE

BB' CROSS-SECTION

TOP SURFACE

CHIP WARPED DUE TO INTERNAL STRESS OF THIN FILM
(WHEN STRESS IS COMPRESSIVE STRESS)

CHIP WARPED DUE TO INTERNAL STRESS OF THIN FILM
(WHEN STRESS IS TENSILE STRESS)

AA' CROSS-SECTION

CHIP WARPED DUE TO INTERNAL STRESS OF THIN FILM

BB' CROSS-SECTION $$\text{RADIUS OF CURVATURE } R = \frac{E \times d^2}{6(1-v) \times \sigma \times t}$$

$E$: SILICON SUBSTRATE YOUNG'S MODULUS
$d$: SILICON SUBSTRATE THICKNESS
$v$: SILICON SUBSTRATE POISSON'S RATIO
$\sigma$: THIN FILM STRESS
$t$: THIN FILM THICKNESS

US 11,502,046 B2

SEMICONDUCTOR CHIP

CLAIM OF PRIORITY

The present application claims priority from Japanese patent application JP2019-146036 filed on Aug. 8, 2019, the content of which is hereby incorporated by reference into this application.

BACKGROUND OF THE INVENTION

The present invention relates to a technology to manufacture semiconductor chips.

WO2012/154211 (Patent Document 1) discloses an assembly method and assembly apparatus for a non-flat device with a curved chip base. Patent Document 1 states that "in one embodiment, a stressed thin film (such as the stressed film layer 207) can be deposited on one or both sides of a thin structure or thin chip, and can deform the chip to a desired degree (bending to some extent, for example). For example, the stressed thin film may be compressed or extended beforehand to be given a bending force in different directions."

SUMMARY OF THE INVENTION

Depending on usage, some semiconductor devices need to be bent in an installation process. One example thereof is an ultrasonic transducer installed on a side surface of a catheter that is to be inserted into a human body. A semiconductor chip made of a large number of ultrasonic transducers is mounted on the surface of the catheter by coiling the semiconductor chip around the catheter, so that the transducers can output ultrasonic waves toward all directions, which allows for a desired measurement to be conducted.

In order to achieve this type of mounting, the semiconductor chip may be made more flexible by reducing the thickness of the semiconductor chip. However, in this case, it would be difficult to handle the semiconductor chip in the process of coiling it around the catheter as it would break more easily. Alternatively, ultrasonic transducer elements may be mounted on the surface of the catheter one by one, but because this would require a larger number of process steps to be conducted, the manufacturing cost would increase.

Patent Document 1 discloses a method to deform a chip to a desired level by utilizing a stressed thin film. Patent Document 1, however, does not describe a specific method for manufacturing such a device. If a manufactured chip needs to be put together with the stressed thin film that has been compressed or extended beforehand, it would be necessary to conduct an assembly process.

In order to solve at least one of the foregoing problems, provided is a semiconductor chip, comprising: a semiconductor substrate; a thin film formed on the semiconductor substrate, the thin film having internal stress; and a semiconductor device formed on the semiconductor substrate that has the thin film formed thereon, wherein the semiconductor chip warps due to the internal stress of the thin film.

According to one embodiment of the present invention, it is possible to manufacture a semiconductor chip with a desired radius of curvature with a simple manner. Challenges, configurations, and effects other than those described above will become apparent in the descriptions of embodiments below.

DETAILED DESCRIPTION OF THE EMBODIMENTS

Below, embodiments of the present invention will be explained with reference to figures.

Figure 1A:
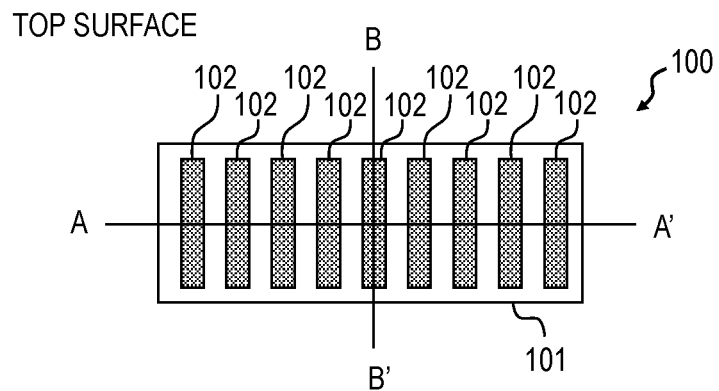
FIGS. 1A to 1C are diagrams for explaining the configuration of a semiconductor chip of an embodiment of the present invention.
Figure 1B:
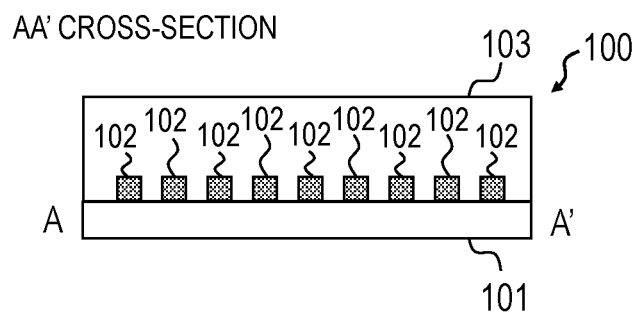
Figure 1C:
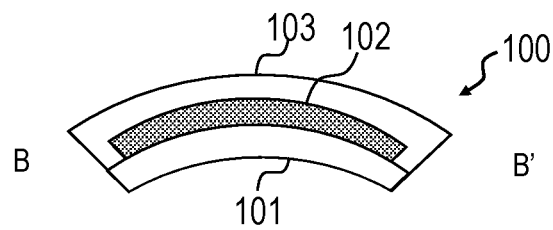

FIGS. 1A to 1C are diagrams for explaining the configuration of a semiconductor chip 100 of an embodiment of the present invention.

Specifically, FIGS. 1A, 1B, and 1C are respectively the planar view, the AA' cross-sectional view, and the BB' cross-sectional view of the semiconductor chip 100 of this embodiment. As illustrated in FIG. 1B, the semiconductor chip 100 of this embodiment includes a semiconductor substrate 101, a plurality of thin films 102 (stressed thin films) formed on the semiconductor substrate 101 and having internal stress, and a semiconductor device 103 formed thereon.

The semiconductor substrate 101 is a common silicon wafer, for example. The thin film 102 may be an insulating film or metal film. The plurality of thin films 102 are aligned in one direction. The size of each thin film 102 in the direction along which the thin films are aligned, and the size thereof in the direction perpendicular to the alignment direction may differ from each other. In the example of FIG. 1A, each thin film 102 takes the form of a rectangle having the shorter side in the alignment direction (the direction parallel to a line that connects A to A' of FIG. 1A, which may also be referred to as the AA' direction below), and the longer side in a direction perpendicular to the alignment direction (the direction parallel to a line that connects B to B' of FIG. 1A, which may also be referred to as the BB' direction below). That is, the size of each thin film 102 in the direction perpendicular to the alignment direction is larger than the size thereof in the alignment direction.

The semiconductor device 103 may be any types of semiconductor device such as a general integrated circuit or MEMS (micro-electro-mechanical systems). As described below, in this embodiment, ultrasonic transducers such as CMUTs (capacitive micro-machined ultrasound transducers) are formed as the semiconductor device 103.

The thin films 102 are formed on the semiconductor substrate so as to have internal stress, which causes the semiconductor chip 100 to warp. In the example of FIG. 1C, because the thin film 102 has compressive stress, the semiconductor chip 100 extends thereby, and upwardly warps such that the top surface (the surface on which the semiconductor device 103 is formed) rises.

The internal stress of the thin film 102 is isotropic, which means that the semiconductor chip 100 may warp in any directions. However, as illustrated in FIG. 1A, the plurality of thin films 102 are arranged along the AA' direction at an predetermined interval, and the longer side of each thin film 102 coincides with the BB' direction, and therefore, the compressive stress in the BB' direction acts on the semiconductor chip 100 such that the semiconductor chip 100 warps over the entire longer side thereof. On the other hand, the compressive stress in the AA' direction acts on the semiconductor chip 100 only within a range that coincides with the shorter side length of each thin film, and the compressive stress is discontinued where the respective thin films 102 are separated. As a result, the semiconductor chip 100 is more likely to warp in the BB' direction or the longer side direction of the thin film 102. That is, the warping of the semiconductor chip 100 is apparent in the BB' cross-sectional view of FIG. 1C, but can hardly be seen in the AA' cross-sectional view of FIG. 1B.

Next, the manufacturing process of the semiconductor chip 100 will be explained. The semiconductor chip 100 is manufactured through the following steps: forming the thin film 102 on the semiconductor substrate 101 (FIGS. 2A to 2C; patterning the formed thin film 102 (FIGS. 2D to 2F); forming a desired semiconductor device 103 on the thin film 102 that has been patterned (FIGS. 2G to 2I); and reducing the thickness of the semiconductor substrate 101 (FIGS. 2J to 2L).

Figure 2A:
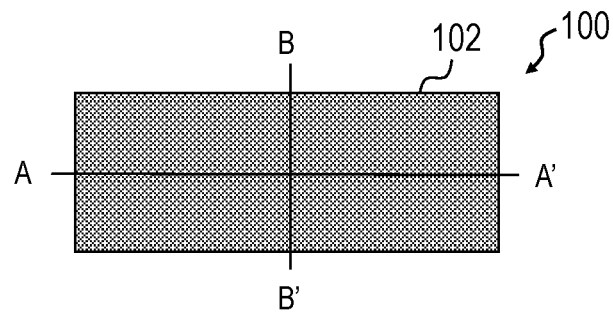
FIGS. 2A to 2C are diagrams for explaining the step of forming a thin film on a semiconductor substrate in the manufacturing process of the semiconductor chip of an embodiment of the present invention.
Figure 2B:
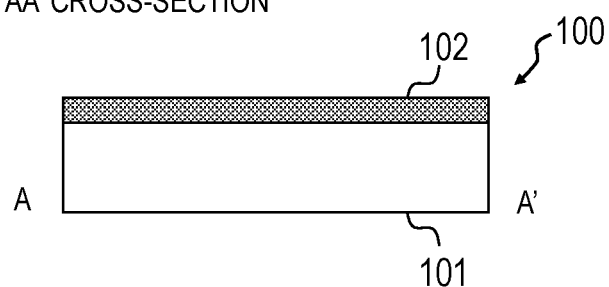
Figure 2C:
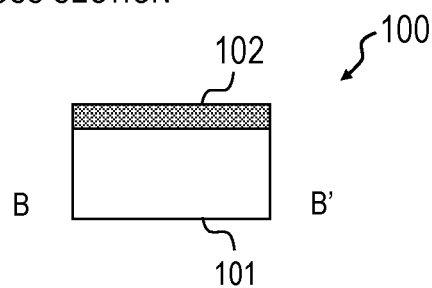

FIGS. 2A to 2C are diagrams for explaining the step of forming the thin film 102 on the semiconductor substrate 101 in the manufacturing process of the semiconductor chip 100 of an embodiment of the present invention.

Specifically, FIGS. 2A, 2B, and 2C are respectively the planar view, the AA' cross-sectional view, and the BB' cross-sectional view of the semiconductor chip 100 when the thin film 102 is formed on the semiconductor substrate 101.

The thin film 102 may be formed of a common material used for a general semiconductor manufacturing process. For example, the thin film 102 may be an insulating film such as silicon dioxide, silicon nitride, or a metal film such as aluminum, tungsten, titanium or titanium nitride. For the method to form the thin film 102, any methods that are used in a general semiconductor manufacturing process such as the CVD (chemical vapor deposition) method and spattering method can be employed for example.

The stress given to the thin film 102 (compressive stress or tensile stress, and the degree of stress) can be adjusted by changing the material of the thin film 102, the film forming temperature, the composition of gas to be used, or the like.

Figure 2D:
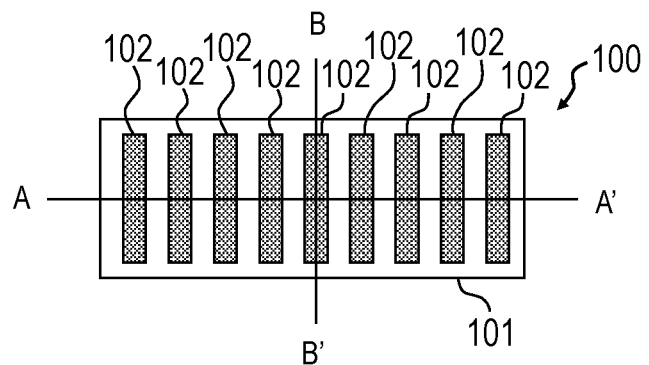
FIGS. 2D to 2F are diagrams for explaining the step of patterning the thin film in the manufacturing process of the semiconductor chip of an embodiment of the present invention.
Figure 2E:
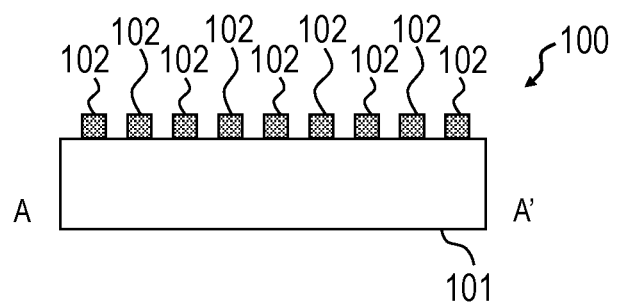
Figure 2F:
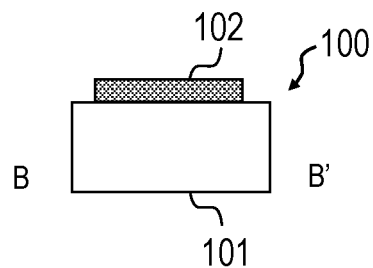

FIGS. 2D to 2F are diagrams for explaining the step of patterning the thin film 102 in the manufacturing process of the semiconductor chip 100 of an embodiment of the present invention.

Specifically, FIGS. 2D, 2E, and 2F are respectively the planar view, the AA' cross-sectional view, and the BB' cross-sectional view of the semiconductor chip 100 when the thin film 102 is patterned. In this example, the thin film 102 is patterned such that rectangles each having the longer side in the BB' direction and the shorter side in the AA' direction are aligned along the AA' direction. This patterning can be conducted by photolithography, which is used for a general semiconductor manufacturing process, for example.

At this point, the semiconductor substrate 101 has a sufficient thickness, and therefore, even when the thin film 102 having internal stress is formed thereon, the semiconductor substrate 101 does not warp almost at all (or in other words, the semiconductor substrate 101 has a sufficiently large radius of curvature). The relationship between the thickness of the semiconductor substrate 101 and the radius of curvature will be explained later (see FIG. 4).

Figure 2G:
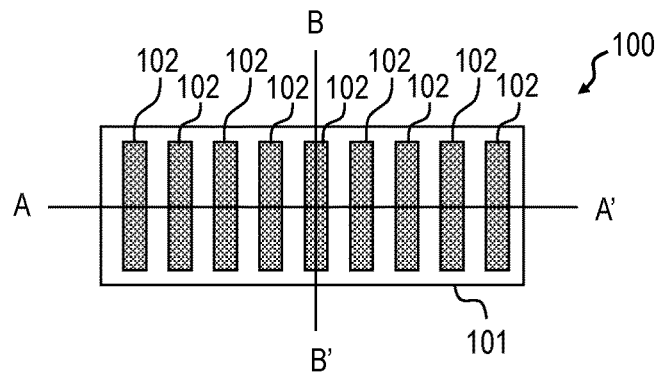
FIGS. 2G to 2I are diagrams for explaining the step of forming a semiconductor device in the manufacturing process of the semiconductor chip of an embodiment of the present invention.
Figure 2H:
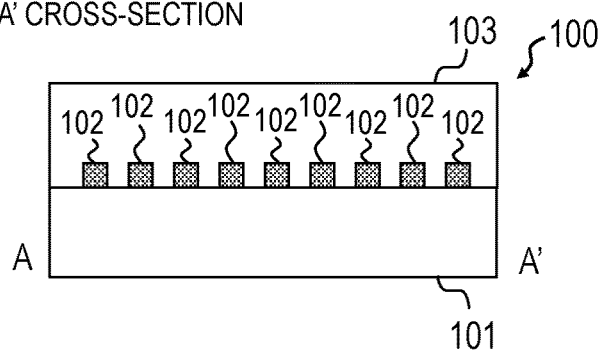
Figure 2I:
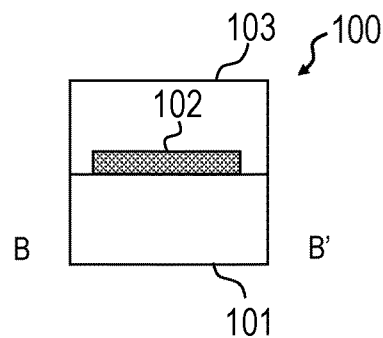
Figure 2J:
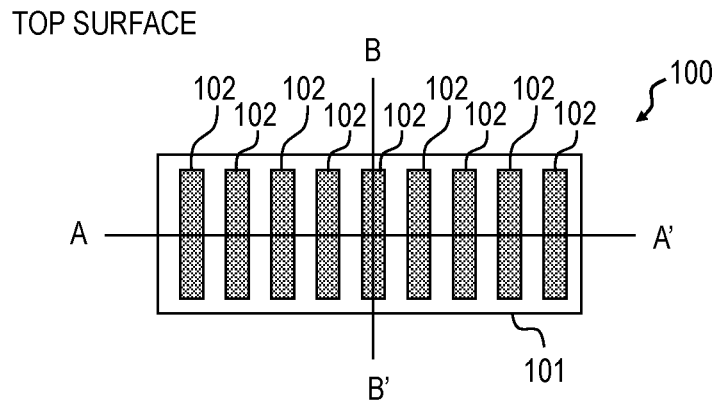
FIGS. 2J to 2L are diagrams for explaining the step of reducing the thickness of the semiconductor substrate in the manufacturing process of the semiconductor chip of an embodiment of the present invention.
Figure 2K:
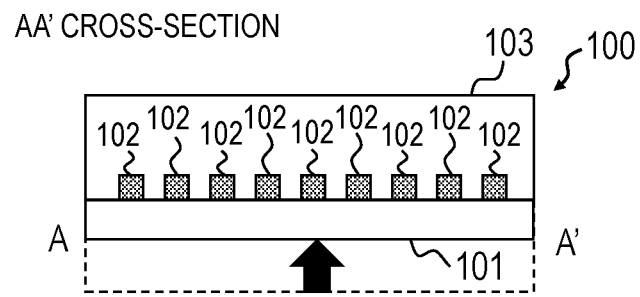
Figure 2L:
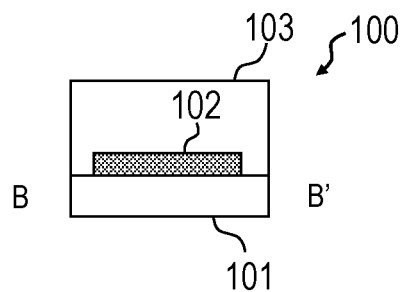

FIGS. 2G to 2I are diagrams for explaining the step of forming the semiconductor device 103 in the manufacturing process of the semiconductor chip 100 of an embodiment of the present invention.

Specifically, FIGS. 2G, 2H, and 2I are respectively the planar view, the AA' cross-sectional view, and the BB' cross-sectional view of the semiconductor chip 100 when the semiconductor device 103 is formed. As described above, any types of semiconductor device may be used for this semiconductor device 103, but in this embodiment, a CMUT is formed. Specifically, a large number of CMUTs are formed so as to be arranged on the semiconductor substrate 101 where the thin films 102 are formed. This semiconductor device 103 such as a CMUT may be formed through a general semiconductor manufacturing process.

FIGS. 2J to 2L are diagrams for explaining the step of reducing the thickness of the semiconductor substrate 101 in the manufacturing process of the semiconductor chip 100 of an embodiment of the present invention.

Specifically, FIGS. 2J, 2K, and 2L are respectively the planar view, the AA' cross-sectional view, and the BB' cross-sectional view of the semiconductor chip 100 in the step of reducing the thickness of the semiconductor substrate 101. There is no special limitation on the method of processing the semiconductor substrate 101 for thickness reduction. For example, the thickness can be reduced by etching the rear surface (or in other words, the side where the thin films 102 are not formed) of the semiconductor substrate 101 in a manner similar to the etching step of a general semiconductor process, or by polishing the rear surface of the substrate 101. As described below, by adjusting the thickness of the semiconductor substrate 101, the semiconductor chip 100 with a desired radius of curvature can be manufactured.

FIGS. 2M to 2P are diagrams for explaining the semiconductor chip 100 manufactured through the manufacturing process of an embodiment of the present invention.

Figure 2M:
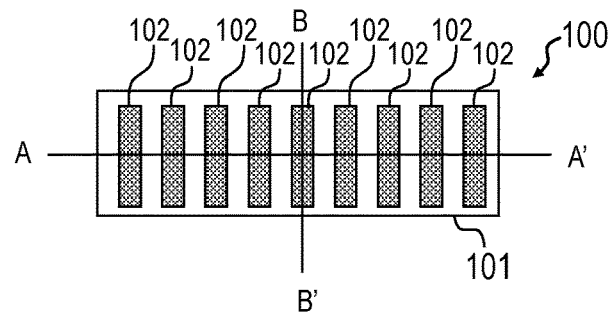
FIGS. 2M to 2P are diagrams for explaining the semiconductor chip manufactured through the manufacturing process of an embodiment of the present invention.
Figure 2N:
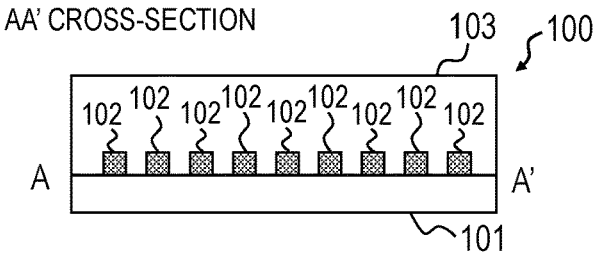
Figure 2O:
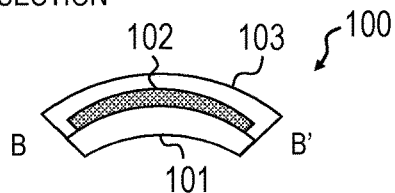
Figure 2P:
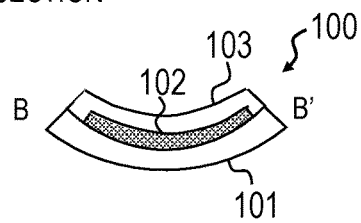

Specifically, FIGS. 2M and 2N are respectively the planar view and the AA' cross-sectional view of the semiconductor chip 100 after the thickness of the semiconductor substrate 101 has been reduced. FIGS. 2O and 2P are both BB' cross-sectional views of the semiconductor chip 100 after the thickness of the semiconductor substrate 101 has been reduced, but the former illustrates the case where the thin film 102 has compressive stress, and the latter illustrates the case where the thin film 102 has tensile stress.

As illustrated in FIG. 2O, when the thin film 102 has compressive stress, the semiconductor chip 100 upwardly warps such that the top surface (or in other words, the side where the semiconductor device 103 is formed) is raised in the BB' cross-sectional view. On the other hand, as illustrated in FIG. 2P, when the thin film 102 has tensile stress, the semiconductor chip 100 downwardly warps such that the bottom surface (or in other words, the side opposite to the semiconductor device 103) sinks in the BR cross-sectional view.

In this example, the thin films 102 are formed such that rectangles each having the longer side in the BB' direction and the shorter side in the AA' direction are aligned along the AA' direction. Thus, as illustrated in FIG. 2N, the warping of the semiconductor chip 100 can hardly be seen in the AA' cross-sectional view.

Figure 3A:
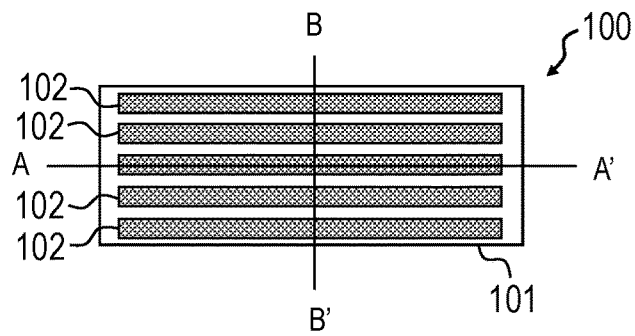
FIGS. 3A to 3C are diagrams for explaining the configuration of a semiconductor chip of a modification example of an embodiment of the present invention.
Figure 3B:
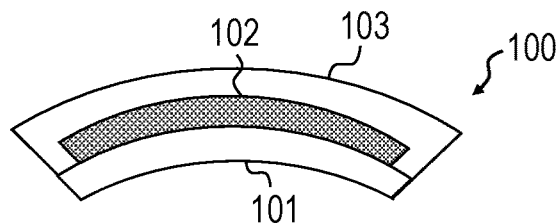
Figure 3C:
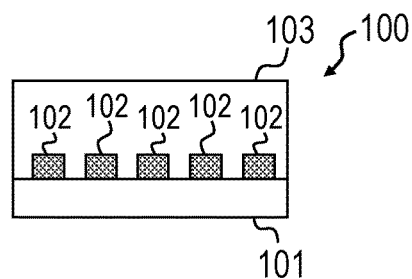

FIGS. 3A to 3C are diagrams for explaining the configuration of a semiconductor chip 100 of a modification example of an embodiment of the present invention.

In the semiconductor chip 100 of FIGS. 1A to 1C, the longer side direction of the semiconductor chip 100 (or in other words, the longer side of the semiconductor substrate 101) intersects with the longer side direction of the patterned thin film 102. Thus, as illustrated in FIGS. 1B and 1C, the manufactured semiconductor chip 100 warps in the shorter side direction.

On the other hand, in the semiconductor chip 100 of FIGS. 3A to 3C, the longer side direction of the semiconductor chip 100 is parallel to the longer side direction of the patterned thin films 102. Thus, as illustrated in FIGS. 3B and 3C, the manufactured semiconductor chip 100 warps in the longer side direction. That is, the warping of the semiconductor chip 100 is apparent in the AA' cross-sectional view of FIG. 3B, but can hardly be seen in the BB' cross-sectional view of FIG. 3C.

The manufacturing process of the semiconductor chip 100 illustrated in FIGS. 3A to 3C is the same as that illustrated in FIGS. 2A to 2P except that the shape of the thin film 102 to be patterned (specifically, the direction of the longer side) is different, and thus, the explanation thereof is omitted.

Figure 4:
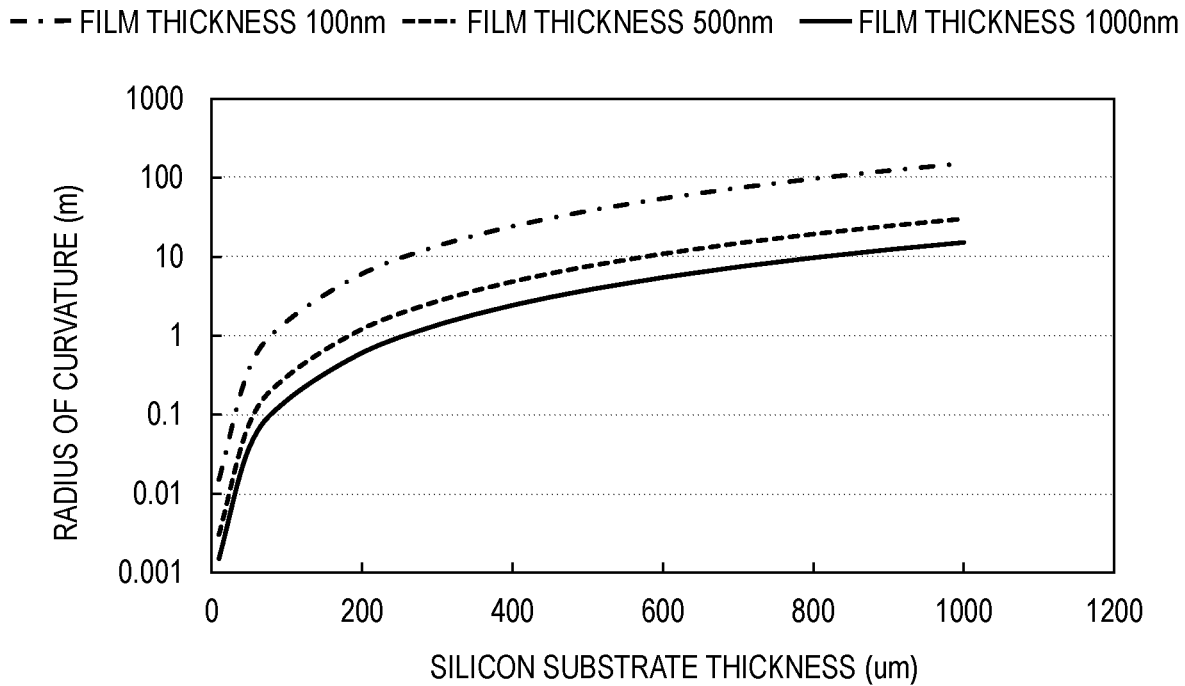
FIG. 4 is a diagram for explaining the relationship between the thickness and the radius of curvature of the semiconductor substrate that is referred to in an embodiment of the present invention.

FIG. 4 is a diagram for explaining the relationship between the thickness and the radius of curvature of the semiconductor substrate 101 that is referred to in an embodiment of the present invention.

The radius of curvature of the warped semiconductor substrate 101 that has the thin film 102 with internal stress formed thereon is calculated by Formula (1) below.

Formula 1

$$\text{Radius of Curvature } R = \frac{E \times d^2}{6(1-v) \times \sigma \times t} \quad (1)$$

Here, E is the Young's modulus of the silicon substrate (that is the semiconductor substrate), d is the thickness of the silicon substrate, v is the Poisson's ratio of the silicon substrate, σ is the stress of the thin film 102, and t is the thickness of the thin film 102.

The graph in FIG. 4 shows the radius of curvature of the warped semiconductor substrate 101 when the thin film 102 with the film stress being 2 GPa is formed on the semiconductor substrate 101, which is calculated by Formula (1) above. The horizontal axis is the thickness of the semiconductor substrate 101, and the vertical axis is the radius of curvature. The solid line, broken line, and one-dot chain line in the graph represent different thicknesses of the thin film 102, respectively corresponding to 1000 nm, 500 nm, and 100 nm.

As described above, by changing the stress of the thin film 102, the thickness of the thin film 102, and the thickness of the semiconductor substrate 101, the radius of curvature can be adjusted in a wide range from approximately 1 mm to approximately 100 m, for example.

Figure 5A:
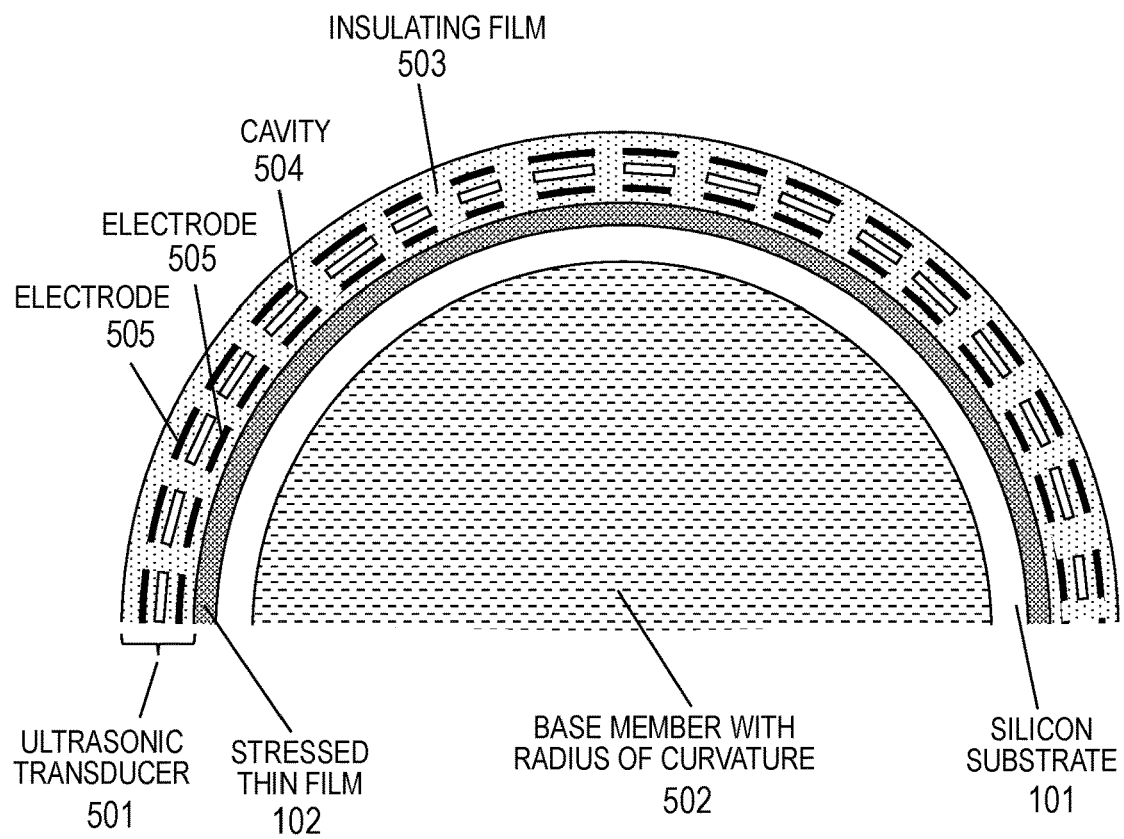
FIG. 5A is a diagram for explaining an application example of the semiconductor chip of an embodiment of the present invention.

FIG. 5A is a diagram for explaining an application example of the semiconductor chip 100 of an embodiment of the present invention.

In this example, an ultrasonic transducer 501 such as a CMUT is used for the semiconductor device 103. In this example, the ultrasonic transducer 501 is a CMUT. In this case, a cell of each ultrasonic transducer 501 (CMUT cell) is constituted of a cavity 504 formed in the insulating film 503, and a pair of electrodes 505 disposed so as to sandwich the cavity 504 from top and bottom. The detailed structure thereof will be explained later with reference to FIG. 5B.

The warped semiconductor chip 100 is mounted onto a base member 502 having a radius of curvature. The base member 502 may be anything, but examples thereof include a catheter that is to be inserted into a blood vessel. As illustrated in FIG. 5A, by wrapping the semiconductor chip 100, which has a large number of CMUT cells arranged thereof, around the base member 502, it is possible to transmit ultrasonic waves to all directions of the catheter and to receive the reflection thereof. This makes it easier to detect a plaque or the like on the inner wall of the blood vessel, for example.

If the base member 502 is a catheter inserted into a blood vessel, then the radius of curvature is approximately 1 mm. According to this embodiment, by adjusting the thickness and the like of the semiconductor substrate 101 as illustrated in FIG. 4, the semiconductor chip 100 can be manufactured such that the radius of curvature thereof is at approximately the same level as that of the base member 502, and the semiconductor chip 100 can be mounted on the surface of the base member 502. This way, it is possible to assemble a catheter on which a large number of CMUT cells are arranged in a simple manner, without causing any damage or without requiring efforts to attach the CMUT cells one by one.

Figure 5B:
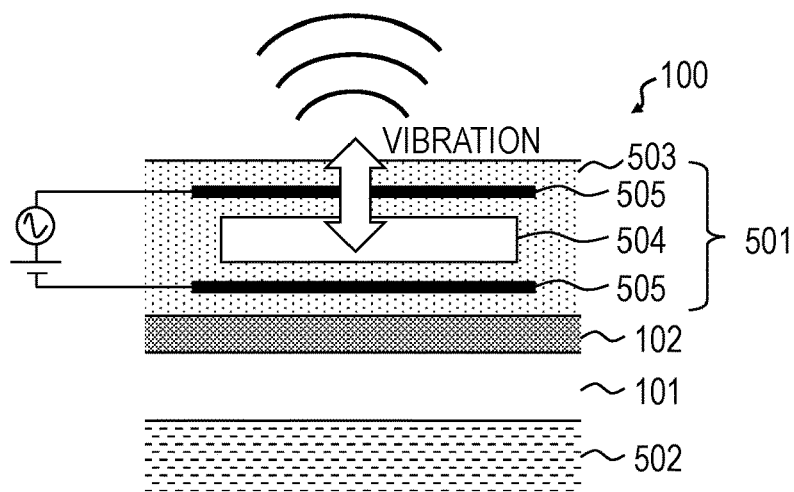
FIG. 5B is a diagram for explaining the structure of the ultrasonic transducer in the application example of a semiconductor chip of an embodiment of the present invention.

FIG. 5B is a diagram for explaining the structure of the ultrasonic transducer 501 in the application example of the semiconductor chip 100 of an embodiment of the present invention.

In this example, a CMUT cell, which is an example of a cell of the ultrasonic transducer 501, is constituted of a cavity 504 formed in the insulating film 503, and a pair of electrodes 505 disposed so as to sandwich the cavity 504 from top and bottom. The pair of electrodes 505 is applied with a voltage obtained by superimposing a DC bias voltage with an AC voltage. This generates an electrostatic force between the upper and lower electrodes 505, and causes the upper electrode 505 over the cavity 504 to vibrate, and as a result, an ultrasonic signal is transmitted.

On the other hand, when an ultrasonic signal is received, the upper electrode 505 over the cavity 504 is caused to vibrate by the received ultrasonic signal, and the resultant potential change of the electrode 505 is detected as a change in capacitance.

Figure 6:
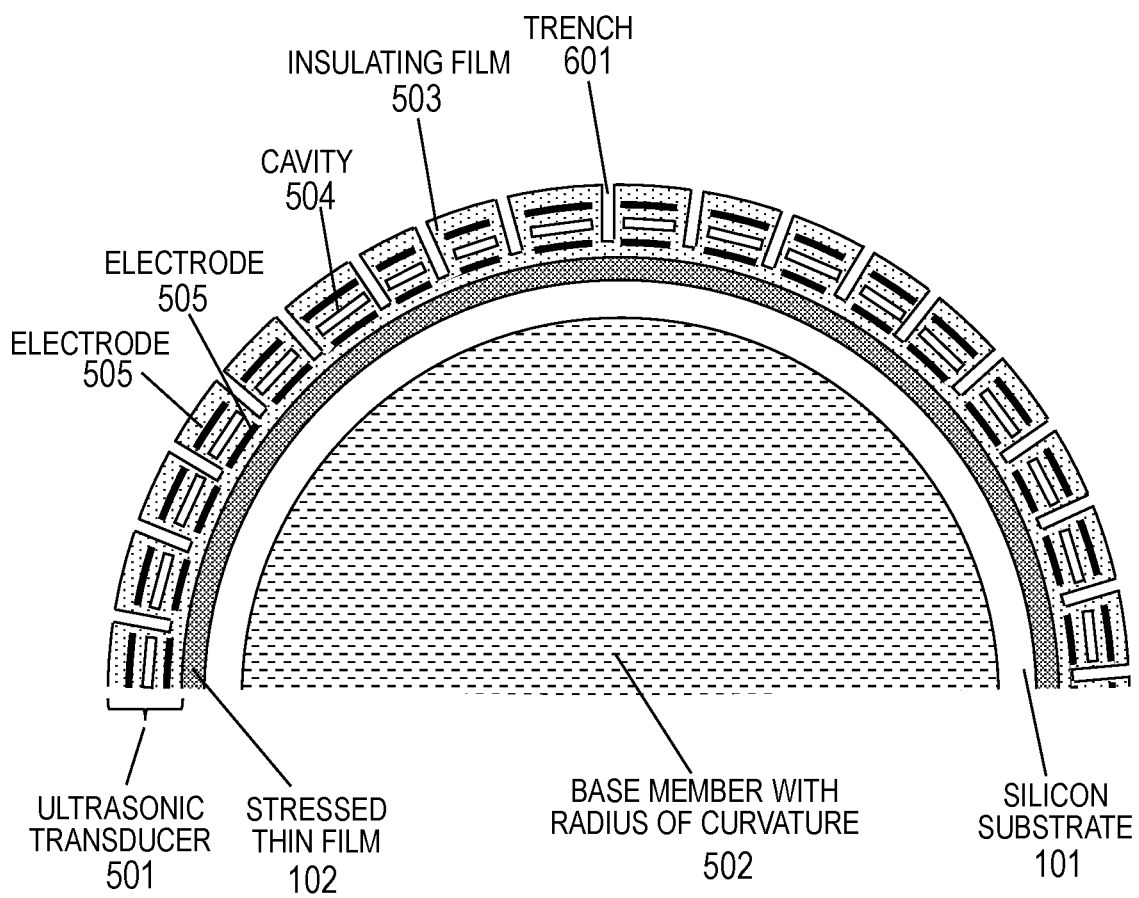
FIG. 6 is a diagram for explaining a modification example of the application example of the semiconductor chip of an embodiment of the present invention.

FIG. 6 is a diagram for explaining a modification example of the application example of the semiconductor chip 100 of an embodiment of the present invention.

The semiconductor chip 100 illustrated in FIG. 6 is the same as that of FIG. 5A except that trenches 601 are formed in the layer of the semiconductor device 103. The trenches 601 are formed at locations that separate the respective CMUT cells from each other as illustrated in FIG. 6. When the semiconductor chip 100 warps, internal stress occurs in the layer of the semiconductor device 103, which could affect the property of the CMUT cells. However, if the trenches 601 are formed as illustrated in FIG. 6, the internal stress in the layer of the semiconductor device 103 would be divided, which could reduce impact on the property of the CMUT cell.

In FIGS. 5A to 6, the CMUT was used as an example of the ultrasonic transducer, and the CMUT may be replaced with a PMUT (piezoelectric micro-machined ultrasound transducer). Alternatively, the CMUT may be replaced with any MEMS or any integrated circuits other than ultrasonic transducers.

What is claimed is:

1. A semiconductor chip, comprising:
   a semiconductor substrate;
   a thin film formed on the semiconductor substrate, the thin film having internal stress; and
   a semiconductor device formed on the semiconductor substrate that has the thin film formed thereon,
   wherein the semiconductor chip warps due to the internal stress of the thin film.

2. The semiconductor chip according to claim 1, wherein the thin film is formed in contact with the semiconductor substrate.

3. The semiconductor chip according to claim 1, wherein a pattern of a plurality of the thin films is formed on the semiconductor substrate, the plurality of the thin films being arranged along a direction perpendicular to a warping direction.

4. The semiconductor chip according to claim 3, wherein a size of each of the thin films in the warping direction of the semiconductor chip is larger than that in a direction perpendicular to the warping direction of the semiconductor chip.

5. The semiconductor chip according to claim 1, wherein the semiconductor device is a capacitive micromachined ultrasonic transducer.

6. The semiconductor chip according to claim 5, wherein a plurality of cells of the capacitive micromachined ultrasonic transducer is formed in a layer where the semiconductor device is to be formed, and
   wherein a trench is formed in the layer where the semiconductor device is to be formed at a position that separates the plurality of cells from each other.

* * * * *